(12) United States Patent
Garbati et al.

(10) Patent No.: US 9,700,539 B2
(45) Date of Patent: Jul. 11, 2017

(54) THERAPEUTIC APPLICATION OF (BOC)$_2$-CREATINE

(71) Applicant: UNIVERSITA' DEGLI STUDI DI GENOVA, Genoa (IT)

(72) Inventors: Patrizia Garbati, Savona (IT); Maurizio Balestrino, Genoa (IT); Enrico Adriano, Genoa (IT); Silvia Ravera, Genoa (IT); Enrico Millo, Genoa (IT); Gianluca Damonte, Genoa (IT); Annalisa Salis, Savona (IT)

(73) Assignee: UNIVERSITA' DEGLI STUDI DI GENOVA, Genoa (IT)

( * ) Notice: Subject to any disclaimer, the term of this patent is extended or adjusted under 35 U.S.C. 154(b) by 0 days.

(21) Appl. No.: 15/107,398

(22) PCT Filed: Dec. 23, 2014

(86) PCT No.: PCT/IB2014/067261
§ 371 (c)(1),
(2) Date: Jun. 22, 2016

(87) PCT Pub. No.: WO2015/097660
PCT Pub. Date: Jul. 2, 2015

(65) Prior Publication Data
US 2017/0000757 A1 Jan. 5, 2017

(30) Foreign Application Priority Data
Dec. 24, 2013 (IT) .............................. TO2013A1070

(51) Int. Cl.
*A61K 31/325* (2006.01)
*A61K 45/06* (2006.01)
*A61K 31/27* (2006.01)

(52) U.S. Cl.
CPC ............ *A61K 31/325* (2013.01); *A61K 31/27* (2013.01); *A61K 45/06* (2013.01)

(58) Field of Classification Search
CPC ....... A61K 31/325; A61K 45/06; A61K 31/27
See application file for complete search history.

(56) References Cited

U.S. PATENT DOCUMENTS

2015/0368192 A1   12/2015   Millo et al.

OTHER PUBLICATIONS

Bergmeyer, H. et al., "Methods of Enzymatic Analysis", Verlag Chemie-Academic Press, (1974), II: 176-178.
Bergnes, G. et al., "Creatine and Phosphocreatine Analogs: Anticancer Activity and Enzymatic Analysis", Oncology Research, (1996), 8(3): 121-130.
De Andrade, R. et al., "Inhibition of creatine kinase activity by 3-butyl-1-phenyl-2-(phenyltelluro)oct-en-1-one in the cerebral cortex and cerebellum of young rats", Journal of Applied Toxicology, (2010), 30: 611-616.
De Andrade, R. et al., "Kinetic studies on the inhibition of creatine kinase activity by 3-butyl-1-phenyl-2-(phenyltelluro)oct-en-1-one in the cerebral cortex of rats", Food and Chemical Toxicology, (2012), 50: 3468-3474.

(Continued)

*Primary Examiner* — Savitha Rao
(74) *Attorney, Agent, or Firm* — Merchant & Gould P.C.

(57) ABSTRACT

A creatine derivative, (Boc)$_2$-creatine, is used as a medicament, in particular in a therapeutic antitumor treatment. I (Boc)$_2$-creatine.

6 Claims, 3 Drawing Sheets

(56) References Cited

OTHER PUBLICATIONS

Garbati, R et al., "A new method to synthesize creatine derivative", Amino Acids,(2013), 45:821-831.
Griffiths, J., "Creatine kinase Isoenzyme 1", Clinics in Labratory Medicine, (1982), 2(3): 493-506.
Joseph, J. et al., "Creatine kinase activity and isoenzymes in lung, colon and liver carcinomas", British Journal of Cancer, (1997), 76(5): 600-605.
Kaddurah-Daouk, R. et al., "Induction of a Cellular Enzyme for Energy Metabolism by Transforming Domains of Adenovirus E1a", Molecular and Cellular Biology, (1990), 10(4): 1476-1483.
Kristensen, C. et al., "Creatine and cyclocreatine treatment of human colon adenocarcinoma xenografts: 31P and 1H magnetic resonance spectroscopic studies", British Journal of Cancer, (1999), 79(2): 278-285.
Li, X. et al., "Knockdown of creatine kinase B inhibits ovarian cancer progression by decreasing glycolysis", The International Journal of Biochemistry & Cell Biology, (2013), 45(5): 979-986.
Lillie, J. et al., "Cyclocreatine (1-Carboxymethyl-2-iminoimidazolidine) Inhibits Growth of a Broad Spectrum of Cancer Cells Derived from Solid Tumors", Cancer Res, (1993), 53: 3172-3178.
Martin, K. et al., "Cell Cycle Studies of Cyclocreatine, a New Anticancer Agent", Cancer Research, (1994), 54(19): 5160-5165.
Ren, J. et al., "Creatine Kinase Inhibitor Iodoacetamide Antagonizes Calcium-Stimulated Inotropy in Cardiomyocytes", Clinical and Experimental Pharmacology and Physiology, (2009), 36: 141-145.
Rodriguez, P. et al., "Importance of Creatine Kinase Activity for Functional Recovery of Myocardium After Ischemia-Reperfusion Challenge", (2003), 41: 97-104.
Saks, V. et al., "Studies of Energy Transport in Heart Cells. Mitochondrial Isoenzyme of Creatine Phosphokinase: Kinetic Properties and Regulatory Action of Mg2+ Ions", Eur. J. Biochem., (1975), 57: 273-290.
Seraydarian, M. et al., "The role of creatine-phosphorylcreatine system in muscle", Journal of Molecular and Cellular Cardiology, (1976), 8(10): 741-746.
Stallings, R. et al., "Human Creatine Kinase Genes on Chromosomes 15 and 19, and Proximity of the Gene for the Muscle Form to the Genes for Apolipoprotein C2 and Excision Repair", Am. J. Hum. Genet., (1988), 43(2): 144-151.
Wallimann, T. et al., "Intracellular compartmentation, structure and function of creatine kinase isoenzymes in tissues with high and fluctuating energy demands: the "phosphocreatine circuit" for cellular energy homeostasis", Biochem. J., (1992), 281: 21-40.
Wyss, M. et al., "Mitochondrial creatine kinase: a key enzyme of aerobic energy metabolism", Biochim Biophys Acta., (1992), 1102(2): 119-166.
Yarema, M. et al., "Acute Tellurium Toxicity from Ingestion of Metal-Oxidizing Solutions", Pediatrics, (2005), 116: 319-321.
Zhang, Y. et al., "Regulation of T Cell Development and Activation by Creatine Kinase B", PLoS One, (2009), 4(4): 1-13.
International Search Report and Written Opinion of the International Search Authority for corresponding International Patent Application No. PCT/IB2014/067261 mailed Apr. 17, 2015, 8 pgs.

THERAPEUTIC APPLICATION OF (BOC)₂-CREATINE

This application is a National Stage Application of PCT/IB2014/067261, filed 23 Dec. 2014, which claims benefit of Serial No. TO2013A001070, filed 24 Dec. 2013, and which applications are incorporated herein by reference. To the extent appropriate, a claim of priority is made to each of the above disclosed applications.

BACKGROUND OF THE INVENTION

The present invention generally falls within the therapeutic field and more particularly within the field of therapy for neoplastic pathologies.

The enzyme creatine kinase (EC 2.7.3.2, CK) plays an essential role in the energy metabolism of cells (Saks et al 1975; Seraydarian and Abbott 1976). The said enzyme is ubiquitous and capable of transferring phosphate groups from ATP to creatine and from phosphocreatine to ADP, allowing for the recharging of ATP. In the proximity of mitochondria, the enzyme creatine kinase catalyzes the phosphorylation of creatine, thereby generating ADP and phosphocreatine. In the cell areas that require more energy, creatine kinase transfers the phosphate group from phosphocreatine to ADP to restore ATP, thus supporting the cell's energy requirements.

The enzyme creatine kinase has a molecular weight of approximately 60 KDa and is made of four subunits: two cytosolic, M-CK and B-CK, and two mitochondrial, "ubiquitous" uMt-CK and "sarcomeric" sMt-CK (Joseph et al 1997; Griffiths 1982).

The two cytosolic subunits are the M (from muscle) subunit and the B (from brain) subunit. The genes that express them are distributed on two different chromosomes: chromosome 14q32 for subunit B and chromosome 19q13 for subunit M (Stallings et al 1988). The combination thereof leads to three different isoforms expressed in the districts that re quire more energy (Walliman et al 1992; Wyss et al 1992): the muscle isoenzyme (CK-MM), the heart isoenzyme (CK-MB) and the brain isoenzyme (CK-BB). The three isoenzymes catalyze the same reaction, namely the reversible transfer of the ATP gamma-phosphate group to the guanidine group of creatine, thereby obtaining phosphocreatine and ADP.

A number of studies have demonstrated that the activity of the creatine kinase enzyme is involved in the growth of cancer (Joseph et al 1997; Li et al 2013; Zhang et al 2009), with its several isoenzymes having different roles in the neoplastic tissues (Kristensen et al 1999). For instance, the brain isoenzyme (CK-BB) was shown to be involved in the tumorigenesis process (Kaddurah-Daouk et al 1990).

A few chemical inhibitors of the creatine kinase enzyme are known. Iodoacetamide is an, alkylating agent that provides complete and irreversible inhibition on the enzyme (Rodriguez et al 2003; Ren et al 2009). The 3-butyl-1-phenyl-2-(phenyltelluro)oct-en-1-one is an α-β-unsaturated ketone used in various industrial productions and as an anti-detonating additive in petrol (Fairhill 1969; Yarema and Curry 2005). It is a competitive inhibitor of the creatine kinase enzyme (De Andrade et al 2010; De Andrade et at 2012).

In consideration of the role played by creatine kinase in the development of cancer, the use of cyclocreatine as treatment against cancer has been studied (Martin et al 1994). This molecule has been found suitable for inhibiting tumor cell lines that express a high level of creatine kinase (Lillie et al 1993). The antitumor action of other creatine analogues has also been assessed (Bergnes et al 1996).

SUMMARY OF THE INVENTION

Creatine derivatives studied so far for the inhibition of creatine kinase, however, present the inconvenience of a non-modulable and irreversible inhibition of the enzyme.

In order to overcome this and other problems of the prior art, the present invention now provides a new antitumor agent which can inhibit the creatine kinase enzyme in a reversible and modulable manner, (Boc)₂-creatine. These properties make (Boc)₂-creatine particularly advantageous in cancer therapy since it can inhibit cell growth in a modulable and reversible manner, blocking the creatine kinase enzyme, the cell's source of energy. An important aspect is that the block caused by (Boc)₂-creatine can be modulated according to need, as far as the total block of the enzymatic activity.

(Boc)₂-creatine is a creatine derivative obtained by chemical synthesis (Millo et al 2012; Garbati et al 2013), which presents 2 t-Boc groups (tert-butoxycarbonyl) on the guanidine group. The formula of the structure of (Boc)₂-creatine is shown below:

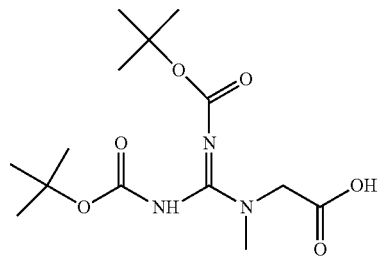 [SMILES: CN(CC(=O)O)C(=NC(=O)OC(C)(C)C)NC(=O)OC(C)(C)C]

The (Boc)₂-creatine used by the present inventors in the experiments described below was synthesized according to the method described in the Italian patent application TO2012 A001098 filed on 18 Dec. 2012.

The present inventors have checked that (Boc)₂-creatine is effective as a modulable blocking agent of the creatine kinase enzyme. This action on the creatine kinase enzyme makes (Boc)₂-creatine a particularly promising molecule as a drug with an antineoplastic action, since the enzyme can be subjected to the desired degree of inhibition by modifying the concentration of the (Boc)₂-creatine.

To the best of the inventors' knowledge, no therapeutic use of (Boc)₂-creatine has yet been described.

DETAILED DESCRIPTION OF THE PREFERRED EMBODIMENTS

A first aspect of the present invention is therefore (Boc)$_2$-creatine for use as a medicament.

A second aspect of the present invention is (Boc)$_2$-creatine for use in the treatment of tumor diseases.

For these purposes, (Boc)$_2$-creatine can be administered alone or in combination with one or more other antitumor agents. Non-limiting examples of other antitumor agents that can be used in combination with (Boc)$_2$-creatine include: alkylating agents such as cisplatin and melphalan, derivatives of cyclophosphamide and carmustine. (Boc)$_2$-creatine or the combination of (Boc)$_2$-creatine with one or more other antitumor agents can be administered to the patient in a suitable form of pharmaceutical dosage comprising conventional excipients and vehicles of pharmaceutical technology and by various means of administration, including, without limitation, the topical, enteral and parenteral routes. The amount of (Boc)$_2$-creatine administered, optionally in combination with one or more other antitumor agents, is a therapeutically effective amount, i.e. capable of producing in the patient the desired effect of inhibiting the creatine kinase enzyme and therefore of inhibiting or reducing the cell proliferation. According to the experiments carried out by the present inventors and illustrated below, a therapeutically effective amount is a quantity which can give a concentration of (Boc)$_2$-creatine of between 0.25 mM and <2 mM, preferably included in the range between 0.25 mM and 1.9 mM, or between 0.25 mM and 1.7 mM, or 0.25 mM and 1.5 mM, or 25 mM and 1.3 mM, more preferably between 0.25 mM and 1 mM. Of course, the effective amount of (Boc)$_2$-creatine to be administered will depend on various factors such as, for example, the patient's weight and age, the type and severity of the disease to be treated, other medical parameters, as well as the desired purpose of the treatment.

The examples below are given for merely illustrative purposes and must not be considered as limiting the scope of the invention.

EXAMPLES

Methods

Activity of the Creatine Kinase Enzyme in the Presence of (Boc)$_2$-Creatine

The activity of the creatine kinase enzyme was measured by the enzymatic coupling method (Bergmeyer 1974). In this method, the ATP hydrolysis is coupled with the NADH oxidation, which is monitored, by means of a spectrophotometer, by the decrease in absorbance at 340 nm ($\epsilon 340 = 6.22$ mM$^{-1}$ cm$^{-1}$).

Figure 1:
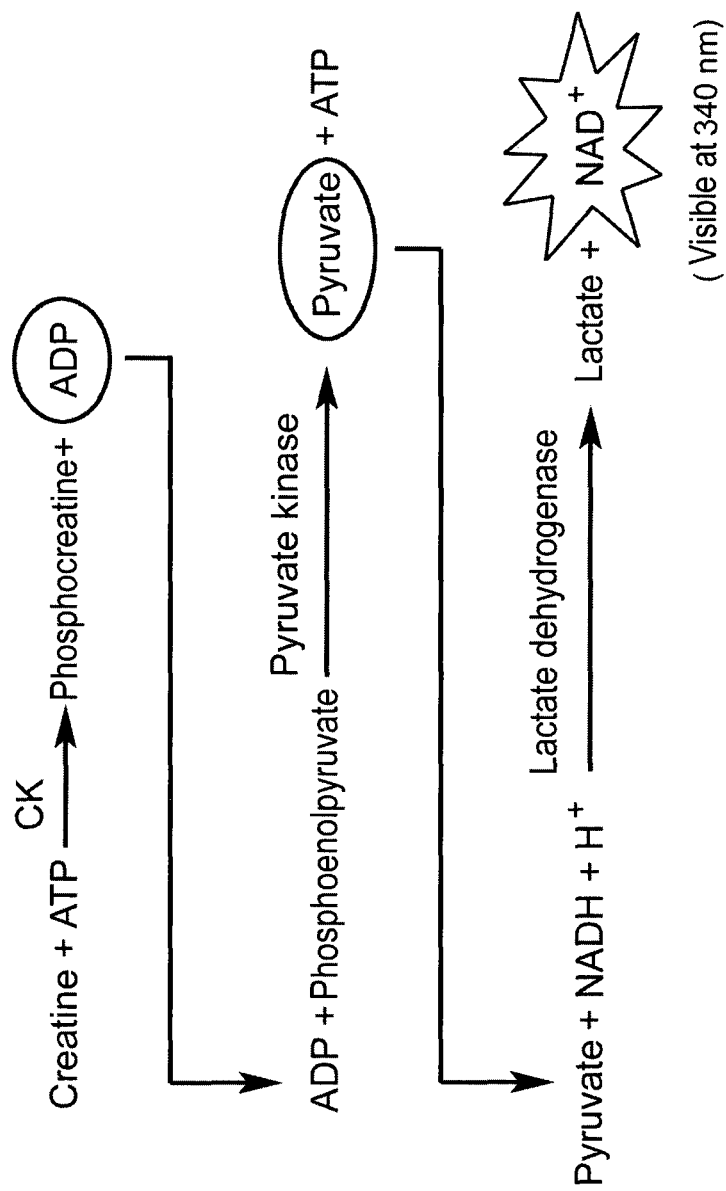
FIG. 1 shows a reaction scheme of the coupled method for the dosage of the creatine kinase enzyme (CK), wherein creatine is phosphorylated to phosphocreatine by CK in the presence of ATP and the reaction of CK is combined with two other enzymatic reactions catalyzed respectively by the pyruvate kinase and by the lactate dehydrogenase.

Dosage of the Creatine Kinase Enzyme and Determination of its Kinetic Constants in the Presence of (Boc)$_2$-Creatine The dosage of the creatine kinase was carried out with the spectrophotometer at 340 nm, following the oxidation of the pyridine coenzyme NADH, which is expressed as a decrease in the absorbance. To be able to carry out the dosage, the reaction of the creatine kinase was combined with two other enzymatic reactions catalyzed respectively by the pyruvate kinase and by the lactate dehydrogenase (Bergmeyer 1974). This method, defined as the coupled method, is necessary because both the substrata and the products of the creatine kinase are not directly visible to the spectrophotometer. In particular, the dosage solution contained the following compounds: 100 mM Tris HCl, pH 7.5, 2 mM MgCl$_2$, 75 mM KCl, 2 mM ATP, 0.5 mM phosphoenolpyruvate, 0.16 mM NADH, 10 IU of pyruvate kinase and of lactate dehydrogenase, in a final volume of 1 ml. The reaction begins by the addition of 2 mM of creatine. The dosage is carried out continuously, i.e. the enzyme activity is followed in real time during the development of the reaction. The dosage trend is monitored by a register connected to the spectrophotometer. The reactions take place in the cuvette, as illustrated in FIG. 1.

To verify the inhibiting effect of (Boc)$_2$-creatine, concentrations between 0.25 and 2 mM were added to the dosage solution, before the addition of the creatine.

To identify the type of inhibition, the maximum kinetic speed (V$_{max}$) and the Michaelis Menten constant (K$_m$) were measured. To be able to carry out the experiment, for each concentration of (Boc)$_2$-creatine, the dosage was carried out in the presence of different substratum concentrations (creatine). The data were analyzed with the Lineweaver-Burk double-reciprocal plot.

Results

Figure 2:
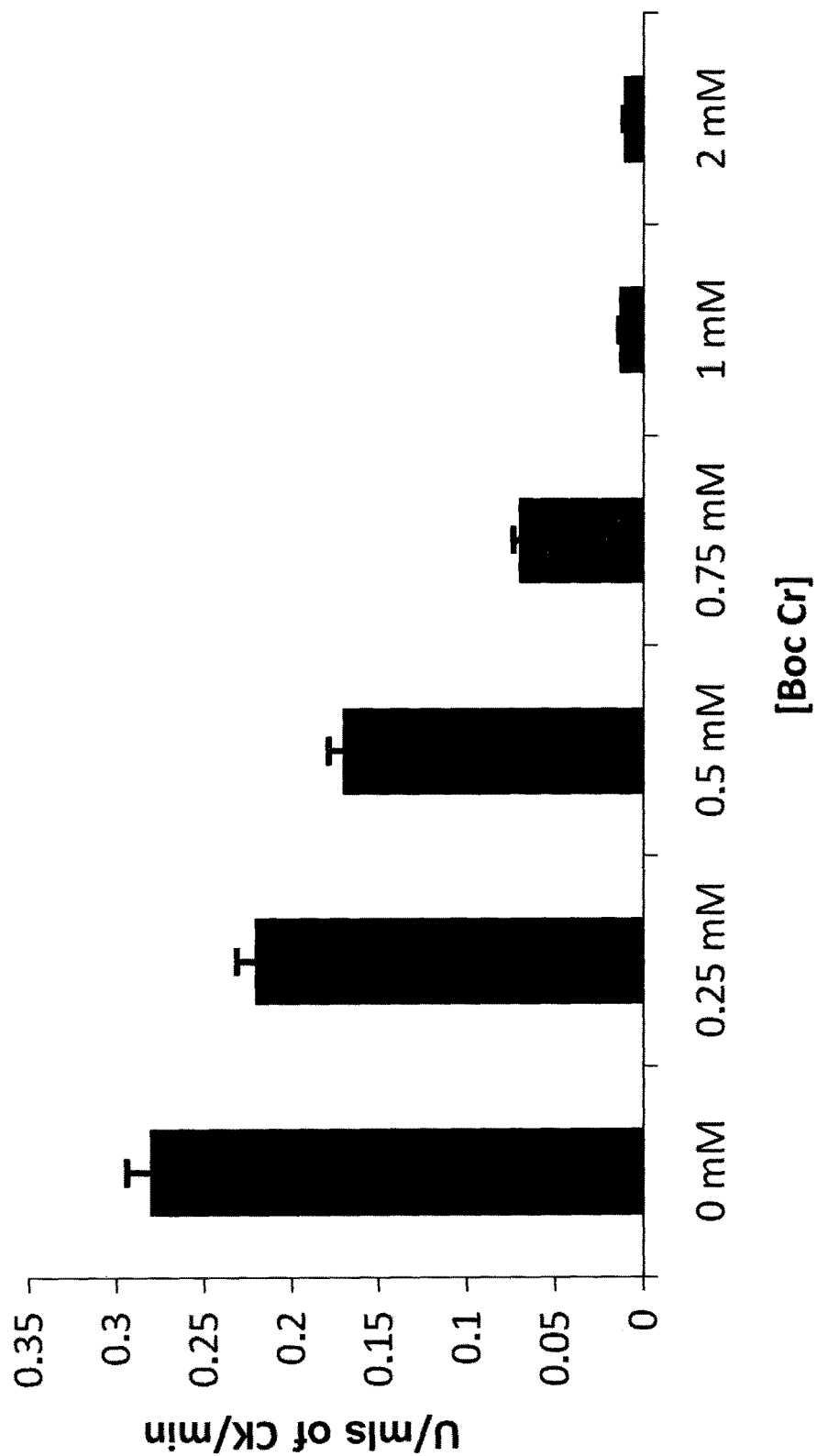
FIG. 2 shows a bar diagram of creatine kinase (CK) activity (expressed as U/ml/min) as a function of (Boc)2-creatine concentration (mM).

From FIG. 2 it can be observed that the maximum inhibition (95%) of the creatine kinase is obtained with 1 mM of (Boc)$_2$-creatine. However, already at a concentration of (Boc)$_2$-creatine equal to 0.25 mM an inhibition of 21% can be observed, which progressively in creases to 39% and to 75% when the concentration of (Boc)$_2$-creatine used is respectively 0.5 mM or 0.75 mM. These data confirm that the inhibition of the enzyme can be modulated, using different concentrations of (Boc)$_2$-creatine.

To understand what type of inhibition the (Boc)$_2$-creatine causes to the creatine kinase enzyme, other experiments were carried out varying both the concentration of the (Boc)$_2$-creatine (0 mM; 5 mM; 1 mM) and the concentration of creatine (the substratum of the enzyme; between 0 and 2 mM). As can be observed in FIG. 3, the inhibition caused by (Boc)$_2$-creatine is of the competitive type because it does not interfere with the maximum speed (V$_{max}$; intercept of the y axis) of the enzymatic catalysis, but it affects the capacity to bind the substratum to the active site of the enzyme (K$_m$; intercept of the x axis). In other words, the (Boc)$_2$-creatine competes with the creatine to bind to the site of the creatine kinase enzyme and thus slows down its activity.

Figure 3:
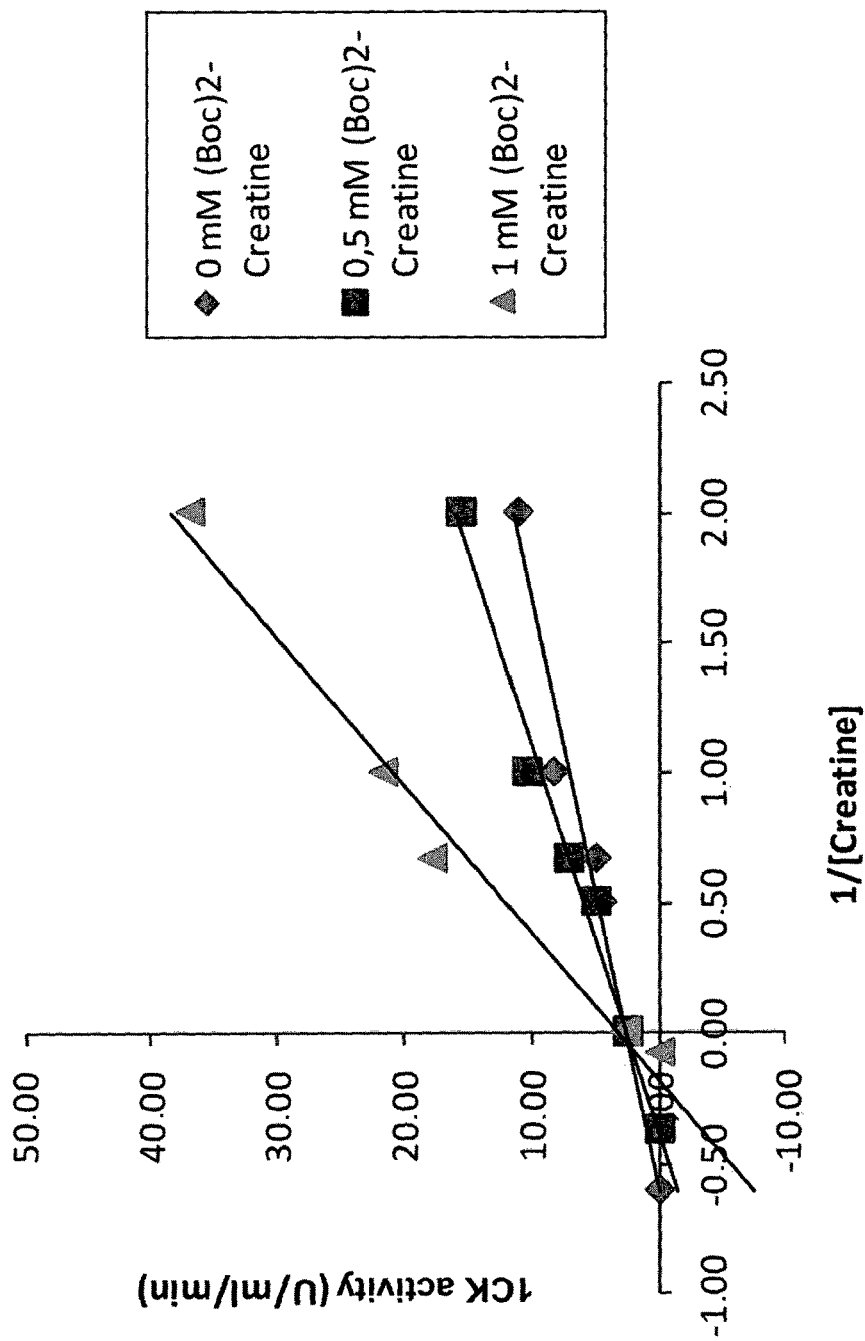
FIG. 3 shows a linear diagram of creatine kinase activity (expressed as U/ml/min) as a function of the inverse of creatine concentration, in the presence of different concentrations of (Boc)2-creatine (mM)

The graph in FIG. 3 allows for identifying two of the most common kinetic enzyme parameters, Maximum speed (V$_{max}$) and the Michaelis-Menten Constant (K$_m$). The first indicates the maximum speed at which the enzyme metabolizes its own substratum over a determined period of time. The second indicates the affinity of the enzyme for the substratum, i.e. the capacity to bind the creatine to the active site. The V$_{max}$ is represented by the reciprocal of the intercept of the Y axis, while the K$_m$ is represented by the negative reciprocal of the intercept of the X axis. As can be observed, even if the concentration of the (Boc)$_2$-creatine varies, the value of the intercept of the Y axis does not change, while the value of the intercept of the X axis does change, increasing in proportion to the concentration of (Boc)$_2$-creatine. This suggests that (Boc)$_2$-creatine competes with the creatine to bind to the active site of the creatine kinase enzyme, causing a competitive type inhibition.

Discussion of the Results

The above-described results show that (Boc)$_2$-creatine is a competitive inhibitor of the creatine kinase enzyme. It binds to the active site of the enzyme, thus preventing the binding of the natural substratum, the creatine. This action results in blocking the enzymatic activity with a consequent cytostatic effect and block of the progression of all the phases of the cell cycle.

Of course, high concentrations of (Boc)$_2$-creatine will have a cytotoxic effect. In fact, slices of mouse hippocampus incubated with 2 mM (Boc)$_2$-creatine for 3 hours at 36° C. show no vital signs. Since tumor development is due to an uncontrolled cellular progression, a molecule which can control the main source of cell energy gives a valid means of controlling cell proliferation.

From the experiments on enzymatic kinetics carried out by the present inventors, it has been deduced that the inhibition of the enzyme takes place in proportion to the concentration of (Boc)$_2$-creatine present. In fact, at a concentration of (Boc)$_2$-creatine equal to 0.25 mM there is an inhibition of 21% and this inhibition increases in proportion to the increase in the concentration of (Boc)$_2$-creatine up to the maximum inhibition (95%) of the creatine kinase which is obtained when the concentration of the molecule rises to 1 mM.

REFERENCES

Bergmeyer H. V. (Ed.). 1974. Methods of Enzymatic Analysis. Verlag Chemie-Academic Press.

Bergnes G, Yuan W, Khandekar V S, O'Keefe M M, Martin K J, Teicher B A, Kaddurah-Daouk R. (1996) Creatine and phosphocreatine analogs: anticancer activity and enzymatic analysis. Oncol Res. 8(3):121-30.

de Andrade R B, Gemelli T, Guerra R B, Funchal C, Wannmacher C M D. (2010) Inhibition of creatine kinase activity by 3-butyl-1-phenyl-2-(phenyltelluro)oct-en-1-one in the cerebral cortex and cerebellum of young rats. J. App. Toxicol. 2010; 30: 611-616. DOI 10.1002/jat.1533 de Andrade R B, Gemelli T, Guerra R B, Funchal C, Wannmacher C M D. (2012) Kinetic studies on the inhibition of creatine kinase activity by 3-butyl-1-phenyl-2-(phenyltelluro)oct-en-1-one in the cerebral cortex of rats. Food and Chemical Toxicology 50:3468-3474

Fairhill L T. 1969. Tellurium. In Industrial Toxicology. Hafner: New York.

Garbati P, Salis A, Adriano E, Galatini A, Damonte G, Balestrino M, Millo E (2013) A new method to synthesize creatine derivatives. Amino Acids 44(6):1-13

Griffiths J C. Creatine kinase isoenzyme 1. Clin Lab Med. 1982 September; 2(3):493-506.

Joseph J, Cardesa A, Carreras J. Creatine kinase activity and isoenzymes in lung, colon and liver carcinomas. Br J Cancer. 1997; 76(5):600-5.

Kaddurah-Daouk R, Lillie J W, Daouk G H, Green M R, Kingston R, Schimmel P. (1990) Induction of a cellular enzyme for energy metabolism by transforming domains of adeno-virus E1a. Mol Cell Biol. 10(4):1476-83.

Kristensen C A, Askenasy N, Jain R K, Koretsky A P. Creatine and cyclocreatine treatment of human colon adenocarcinomaxenografts: 31P and 1H magnetic resonance spectroscopic studies. Br J Cancer. 1999 January; 79(2):278-85.

Li X H, Chen X J, Ou W B, Zhang Q, Lv Z R, Zhan Y, Ma L, Huang T, Yan Y B, Zhou H M. Int J Knock down of creatine kinase B inhibits ovarian cancer progression by decreasing glycolysis. Biochem Cell Biol. 2013 May; 45(5):979-86. doi: 10.1016/j.biocel.2013.02.003. Epub 2013 Feb. 14.

Lillie J W, O'Keefe M, Valinski H, Hamlin H A Jr, Varban M L, Kaddurah-Daouk R. (1993) Cyclocreatine (1-carboxymethyl-2-iminoimidazolidine) inhibits growth of a broad spectrum of cancer cells derived from solid tumors. Cancer Res. 53(13):3172-8.

Martin K J, Winslow E R, Kaddurah-Daouk R. (1994) Cell cycle studies of cyclocreatine, a new anticancer agent. Cancer Res. October 1; 54(19):5160-5.

Millo E, Balestrino M, Damonte G, Garbati P, Adriano E, Salis A (2012) Procedimento per sintetizzare derivati della creatina. Patent number TO2012 A001098

Ren J, Davidoff A J, Ingwall J S. (2009) Creatine kinase inhibitor iodoacetamide antagonized calcium-stimulated ionotropy in cardiomycytes. Clinical and Experimental Pharmacology and Physiology 36:141-145.

Rodriguez P, Avellanal M, Felizola A, Barrigon S. (2003) Importance of creatine kinase activity for functional recovery of myocardium after ischemia-reperfusion challenge. Journal of cardiovascular pharmacology 41:97-104.

Saks, V. A., Chernousova, G. B., Gukovsky, D. E., Smirnov, V. N. & Chazov, E. I. (1975) Studies of energy transport in heart cells. Mitochondrial isoenzyme of creatine phosphokinase: kinetic properties and regulatory action of Mg2+ ions. Eur. J. Biochem. 57, 273-290

Seraydarian M W, Abbott B C. The role of the creatine-phosphorylcreatine system in muscle. J Mol Cell Cardiol. 1976 October; 8(10):741-6.

Stallings R L, Olson E, Strauss A W, Thompson L H, Bachinski L L, Siciliano M J. Human creatine kinase genes on chromosomes 15 and 19, and proximity of the gene for the muscle form to the genes for apolipoprotein C2 and excision repair. Am J Hum Genet. 1988 August; 43(2):144-51.

Wallimann T, Wyss M, Brdiczka D, Nicolay K, Eppenberger H M. (1992) Intracellular compartmentation, structure and function of creatine kinase isoenzymes in tissues with high and fluctuating energy demands: the 'phosphocreatine circuit' for cellular energy homeostasis. Biochem J. 281 (Pt 1):21-40.

Wyss M, Smeitink J, Wevers R A, Wallimann T. (1992) Mitochondrial creatine kinase: a key enzyme of aerobic energy metabolism. Biochim Biophys Acta. 1102(2):119-66

Yarema, M. C., Curry, S. C., 2005. Acute tellurium toxicity from ingestion of metaloxidizing solutions. Pediatrics 116, 319-321.

Zhang Y, Li H, Wang X, Gao X, Liu X. Regulation of T cell development and activation by creatine kinase B. PLoS One. 2009; 4(4):e5000. doi: 10.1371/journal.pone.0005000. Epub 2009 Apr. 1.

The invention claimed is:

1. The compound (Boc)$_2$-creatine in a pharmaceutical dosage form, for use as a creatine kinase inhibitor.

2. The compound (Boc)$_2$-creatine for use according to claim 1, for the treatment of tumor diseases.

3. The compound (Boc)$_2$-creatine for use according to claim 1, in combination with one or more other antitumor agents.

4. The compound (Boc)$_2$-creatine for use according to claim 1, in a concentration within the range of 0.25 mM to <2 mM.

5. The compound (Boc)$_2$-creatine for use according to claim 4, in a concentration within the range of 0.25 mM to 1.9 mM.

6. The compound (Boc)$_2$-creatine for use according to claim 4, in a concentration within the range of 0.25 mM to 1 mM.

* * * * *